United States Patent
Cho et al.

[11] Patent Number: 5,924,996
[45] Date of Patent: Jul. 20, 1999

[54] PROCESS AND DEVICE FOR DETECTING THE EXCHANGE OF HEAT BETWEEN THE HUMAN BODY AND THE INVENTED DEVICE AND ITS CORRELATION TO THE GLUCOSE CONCENTRATION IN HUMAN BLOOD

[75] Inventors: Ok Kyung Cho; Birgit Holzgreve, both of Dortmund, Germany

[73] Assignee: OK Kyung Cho, Dortmund, Germany

[21] Appl. No.: 08/765,252

[22] PCT Filed: Jul. 6, 1995

[86] PCT No.: PCT/DE95/00864

§ 371 Date: Apr. 29, 1997

§ 102(e) Date: Apr. 29, 1997

[87] PCT Pub. No.: WO96/01075

PCT Pub. Date: Jan. 18, 1996

[30] Foreign Application Priority Data

Jul. 6, 1994 [DE] Germany .............................. 44 23 663

[51] Int. Cl.⁶ .................................................... A61B 10/00
[52] U.S. Cl. ............................................. 600/549; 600/365
[58] Field of Search .................................... 600/309, 316, 600/347, 365, 412, 474, 549

[56] References Cited

FOREIGN PATENT DOCUMENTS

| 0 593 415 | 4/1994 | European Pat. Off. . |
|---|---|---|
| 21 05 820 | 4/1972 | Germany . |
| 41 02 640 | 9/1991 | Germany . |
| 43 42 105 | 6/1995 | Germany . |
| 2 203 835 | 10/1988 | United Kingdom . |

OTHER PUBLICATIONS

*Optical Engineering*, "Infrared Radiometry of Thermally Insulated Skin for the Assessment of Skin Blood Flow" by Meir Nitzan et al, Sep. 1994, vol. 33, No. 9, pp. 2953–2956.

*Proceedings of the Ninth Annual Conference of the IEEE Engineering in Medicine and Bilogy Society*, "Microwave Thermal Imaging by Passive Radiometry" by A. Mamouni et al., Nov. 1987, vol. 4, pp. 1935–1936.

*Diabete & Metabolisme*, "Facial and Sublingual Temperature Changes Following Intravenous Glucose Injection in Diabetics" by R.M. Hillson et al., 1982, vol. 8, pp. 15–19.

*Primary Examiner*—Max Hindenburg
*Attorney, Agent, or Firm*—Evenson, McKeown, Edwards & Lenahan, P.L.L.C.

[57] ABSTRACT

A process and device are disclosed for sensing the thermal interaction between the human body and the disclosed device. The thus obtained physical measurement data are electronically converted and may be associated in an appropriate manner to concentrations of certain components of human blood determined in an unambiguous manner, such as cholesterol, triglycerides, etc., in particular glucose. The device has at least one heat measurement unit and electronic control, regulation, evaluation and output units. The device also allows temperature measurements with high spatial and temporal resolutions. The process is non-invasive and is particularly suitable for determining without contact the glucose concentration in parts of the human body, in particular human blood.

34 Claims, 2 Drawing Sheets

PROCESS AND DEVICE FOR DETECTING THE EXCHANGE OF HEAT BETWEEN THE HUMAN BODY AND THE INVENTED DEVICE AND ITS CORRELATION TO THE GLUCOSE CONCENTRATION IN HUMAN BLOOD

BACKGROUND OF THE INVENTION

1. Technical Field

The present invention relates to an electronic device for detecting interaction between the human body and the invented device permitting noninvasive determination of the glucose concentration in parts of the human body, in particular, in the human blood.

2. State of the Art 1.1 Physical Background 1.1.1 Heat and Temperature

Heat or rather thermal energy is the sum of the individual kinetic energy of the components of the material. This mean energy is the same for all particles, although independent of its mass:

$$<W> = \tfrac{1}{2} m <v^2>$$

Temperature is only another measure for the mean kinetic energy of the molecules. If only the translation energy is considered, its mean value is given by $$<W_{trans}> = \tfrac{1}{2} m <v^2> = \tfrac{3}{2} k\, T.$$

In this general definition of temperature m stands for the mass, $<v^2>$ for the square average velocity of the molecules. The Boltzmann constant k has the value of $$k = 1.381 \times 10^{-23} J\, K^{-1}.$$

1.1.2 Temperature Measurement

Fundamentally, a temperature measurement procedure can be based on every known reproducible relationship between a material property and the temperature. In practice, e.g., the expansion of fluids, the change in electric resistors, the change in the sonic velocity in solid bodies, etc. are drawn upon for the measurement of temperature.

1.1.2.1 Thermistors and Thermo-elements

Certain thermistors and thermo-elements are particularly suited, due to their small mechanical dimensions, for temperature measurement within the scope of the present invention.

In most semiconductors, the temperature coefficient of the electric resistance is negative (high-temperature conductor, or "NTC-resistor" or called in short "NTC" <negative temperature coefficient>).

Thermo-elements are the electric thermometers most frequently employed in the temperature range of 1 K to 3000 K. Although the measurement uncertainty is larger than that of the resistors, the thermo-elements are much easier to produce, have small spatial dimensions, possess a short response period and are especially suited for measuring temperature differences. Voltage compensators or high-ohmic voltmeters are employed for measuring the thermo-electric voltage.

1.1.3 Mechanism of Heat Transport

Thermal energy can fundamentally be transported either by radiation, heat conduction or flow (convection).

1.1.3.1 Heat Radiation

Heat radiation is of an electro-magnetical nature such as light. It permits releasing heat even into a vacuum. This release is only dependent on the temperature of the radiating body. Heat radiation is also called temperature radiation or thermal radiation.

1.1.3.2 Heat Flow

Heat flow presupposes macroscopic movements in fluids or gases, the heat content of which is transported in this manner to other sites.

1.1.3.3 Heat Conduction

Heat conduction occurs only in material but is however not connected to its macroscopic movement, but rather to the energy transfer due to the impact between the molecules. It presupposes local differences in the molecular energy, that is, drops in temperature. Frequently, it is the heat transport which sets off this temperature drop that generally results in temporal change of the temperature distribution.

1.1.3.3.1 Heat Conduction in Insulators

In metals, heat like the electric current is transported predominantly via conduction electrons, in the insulators however, heat is transported via phonons. Phonons are respectively quanta (smallest amounts of energy) of elastic lattice vibrations of the wavefield generated therefrom. Just as the heat content of a solid body can be considered the energy of its phonon gas, heat conduction therein occurs as the transport phenomenon in the phonon gas. Thermal energy can be transported in a gas in two ways:

a) as supplementary energy of a flowing gas which is hotter than its surroundings like in a heat exchanger, or b) as energy diffusion in a resting gas while maintaining a temperature gradient, with the gas being in a thermal equilibrium with its surroundings at every site.

Only the second procedure (b) is heat conduction. The heat conductivity is the proportional constant between heat flow and T-gradient.

1.2 Physiological Background 1.2.1 Biological Rhythms of Blood Glucose

Close-mesh blood glucose day and night profiles of normal individuals and ill individuals show similarities such as a rise in the evening, a drop during the night, another rise in the early morning. This is true despite very different external factors such as age, nutrition, illness, etc. These similarities seem to reflect endogenic and vegetative periodicity. Such periodic fluctuations are called circadian rhythms. This refers to biological rhythms with a period length of about 24 hours. This biological rhythm continues even if two important environmental periodicities such as light and ambient temperature are maintained constant.

In a multicell organism, the functions of the entire organism as well as that of the individual organs and cells are subject to rhythms which are in a specific relationship to one another and to the periodicity of the environment and are called "circadian organization". Glycogens, glycogen synthase and glycogen phosphorylase and the corresponding blood glucose concentrations permit detecting a distinct, parallel rhythm.

In humans, the vegative functions such as pulse, blood pressure, respiration, body temperature, etc. also are subject to circadian periodicity. Activity phases, e.g., have durations with individual fluctuations lasting from 0800–1200 and 1600–1900 hours. During this time, metabolism is catabolic. Raised are, e.g., the body temperature, the blood pressure and the blood glucose concentration. During this time, the person is able to work. In contrast, the vagotonic recovery phases are between 1300–1500 and 2200–0600 hours. During these phases, the aforementioned parameters are low and the person is ready to sleep. These phases are subject to time shifts which can be schematically allocated to a morning person or a night person.

1.2.2 Physiology and Regulation of the Body Temperature

The predominant chemical heat producing processes and physical heat loss processes are related in a control circulatory system.

The heat loss processes (physical thermal regulation) were divided into heat conduction, heat radiation, heat flow, evaporation, respiration and secretion. Belonging to the heat producing processes are 1) minimal heat production due to a) essential energy production and b) obligatory heat production; 2) nutrition-inducible heat production; and 3) regulatory heat production with a) increased muscle activity and b) without muscle activity.

As the body always tries to maintain a constant core temperature with changing ambient temperature, the heat production and heat absorption has to be brought into equilibrium with the heat loss.

In order to be able to determine a temperature on the surface of the skin, it is first important to ascertain the amount of heat which passes through the surface of the skin. The greatest part of the heat is dissipated to the surroundings via the skin. The four essential types of heat transfer will be briefly described again.

Heat conduction refers to heat exchange between adjacent site-fixed particles.

Heat convection describes the heat transport of moving particles (blood, air). Heat radiation characterizes every electro-magnetic radiation, in this case temperature radiation without any relay of a material heat carrier. The evaporation, on the other hand, is a measure of the heat transport during the transition from the fluid phase to the gaseous phase.

At room temperature and rest conditions, the greatest part of the heat amounts are released by radiation. The rise in heat production following a meal is caused by nutrition-inducible thermogenesis. This can be explained by ATP loss resulting from the conversion of the ingested nutrients into body-own substances. The influence of humidity on heat regulation has to be taken into account.

Heat flow from the interior to the exterior is composed of two parts. The first part describes the transition core-skin, the second the transition skin-surroundings.

The thickness and thermal conductivity of the media through which the heat is transported as well as the heat transition conditions influence the heat transport. The skin temperature is therefore a function of the interior and exterior heat transport and transition conditions.

Conductive heat transport is only encountered in the top layers of the epidermis. Convective transport with blood predominates in the entire remaining organism. The extremities take on a special position. The heat resistance, between the core and the surface can be set maximally large or minimally small. They act according to the principle of a countercurrent heat exchanger.

The following discusses skin temperature and skin blood circulation. In the zone of metabolic neutrality, the core temperature is regulated by controlling heat loss. The skin temperature changes more steeply here than in other areas.

Below 20° C., blood circulation is minimal and therefore the temperature drop skin-room and heat loss are zero. If the room temperature rises, the increase in blood circulation leads to a rise in skin temperature.

Under constant conditions, core and surface temperature are subject to fluctuations in daily rhythm. The values of the extremities drop by about 4–5° from 0600 am to 1200 noon. However, they then stay at this level. In the evening, the temperature of the extremities rises again. On the other hand, the core temperature rises again until 1800 o'clock and then drops again. The surface temperatures at the head and throat follow the course of the core temperature. Fluctuations in temperature are based on changes in the blood circulation in the skin. The blood circulation in the feet, e.g., in the afternoon is less than at night. Blood circulation on the forehead runs parallel to the core temperature.

SUMMARY OF THE INVENTION

The present invention is based on the striking revelation that there is a great correlation between the circadian fluctuation of the glucose concentration of the human blood and the circadian periodicity of the body temperature measured at specific suitable points. This suggests drawing upon body temperature for determining glucose in the blood.

Thus, the object of the present invention is to build, for the purpose of measuring the temperature of the human body (e.g. surface temperature), a sensor whose measurement accuracy and precision surpasses that of conventional sensors for temperature measurement. Furthermore, the present invention, i.a., has the object to permit temperature measurements having high spatial and temporal resolution.

Therefore, the present invention describes a sensor as well as a process which together permit the exact determination of the concentration of blood glucose in the human body by means of highly precise temperature measurement, and especially in a non-invasive manner, i.e., in a manner that is unharmful to the body and furthermore, under certain preconditions, without touching it. The removal of capillary blood from the fingertips or earlobes usually required for a conventional process for determining blood glucose is therefore obviated.

Moreover, the present invention is based on the fact that numerous heat generating processes of chemical or physicochemical nature take place in the human body. These can be considered as different "heat sources" according to their "origin" and their "site of origin". Each of these heat sources emits a "heat spectrum", i.e., heat radiation with specific frequency ranges, characteristic of it.

The idea and object of the present invention are, therefore, i.a., also to supply a method with the aid of which the aforementioned heat spectrum can be respectively identified and localized to build a sensor permitting frequency selection of the heat radiation radiated into the body.

Processes in the human body in which glucose is transformed in some manner are also accompanied by certain heat producing/consuming processes. A suitable invented mathematical evaluation algorithm operable on a processor permits allocation of measured, selected heat/temperature data to glucose concentrations.

According to the invention, a sensor is generally built in such a manner that it can measure the thermal energy radiating from the object-to-be measured selectively either by means of heat radiation or by means of heat conduction, or by drawing upon a combination of the two mechanisms of heat transfer for measurement.

The heat source (heat transmitter) is a suitable part of the human body, e.g., a finger. The sensor according to the invention serves as a receiver. If heat transmission through heat conduction is to be measured, the finger is brought into contact with the sensor surface by laying it on the sensor. If the heat radiating from the finger is to be measured, the finger is positioned at a defined distance above the sensor surface without touching it. A spacer made of a material with the lowest possible heat conductivity (e.g. styropor) is placed between the sensor surface and the finger. This ensures, if need be, that the prescribed distance between the radiation source and radiation receiver can be reproduced. Suitable spacers which can be placed on the sensor surface can also be designed in a disposable manner, i.e. as a "disposable spacer".

If both the heat conduction and the heat radiation are to be recorded, the sensor is designed in such a manner that, on the one hand, part of its surface is in contact with the finger and, on the other hand, e.g., an indentation in the surface, permits radiation to pass through the free space via a specific, well-defined distance in order to subsequently impinge upon a correspondingly designed site of the sensor.

In a general embodiment, the sensor has a configuration which can take very different forms. The sensor body or the sensor casing, also called the sensor head, have the task of holding the individual components described below, and attaching the components to each other in a specific arrangement and protecting them from destruction and/or soiling.

The so-called sensor area contains (is formed from) at least one so-called feeler for measuring heat conduction. This sensor is a, e.g., cylindrically shaped rod of defined length and defined cross section composed of electrically insulating material of known physical properties, in particular however, having heat conductivity properties suitable for this purpose. Usually, multiple feelers of the same cross section and the same material but of different length as well as feelers of the same cross section and same length but of different material and different heat conductivity are combined in a suitable manner.

An invented sensor can, e.g., contain one or multiple NTC resistors, thermo-electric elements, pyroelectric detectors or combinations of any desired number of the aforementioned elements.

Below (i.e., the circular surface of the cylindrically shaped rod facing away from the finger) each feeler is at least one temperature sensor, e.g., the aforementioned NTC resistor.

Above (i.e., on the side facing the finger) the sensor is situated, if need be, a disk (small plate) made of a material having an especially high heat conductivity, e.g., gold, in order to optimize the heat transfer coupling between the finger and the sensor.

In the region of the feelers, a space which can be irradiated without obstruction by the radiation coming from the finger is created by a suitable device. Between the radiation source and the radiation detector (e.g., NTC) for registering this radiation, usually are arranged filters and lenses made of suitable material, e.g., Ge or Si, as well as shutters or other optical components in any desired number and combination.

The distances between the radiation source and the window, filter, shutter, etc., as well as between the radiation source and the radiation detector are defined. Suitable spacers ensure the reproducibility of these distances. The aforementioned feelers can themselves assume the function of spacers. Likewise, loose, detachable spacers can be designed as disposable one-way spacers.

Thermal interactions can also be calculated using data processing from differences and/or quotients of measured data, which can be relatively calculated using at least one reference value, and from their respective conversations, derivations and integrals. The measurements can be applied only to heat conduction or to weakened heat conduction or to heat radiation alone or to a combination of all those processes. The differences and/or quotients can be obtained by applying at least one of contact and/or contactless measurement process in as precise a manner as possible not only during the measurement of the to-be-measured body itself, but also prior to and following to it. Those data can also be used e.g. as blank values or as data for calibration. The interactions, and/or at least one of a temperature difference or temperature quotient, may then be allocated by a mathematical algorithm unequivocally to the specific glucose concentration of the human blood. In a special case, a temperature difference or quotient may not exceed of ±33K of the measured temperature in or on a casing of the sensor serving as a reference temperature. Additional measurements of specific and/or random sites or of air, gas or vacuum temperature may as well be used as reference and as background respectively. Those measurements may be made prior to or following the measurements of the to-be-measured body itself. Interfering room temperature may be compensated during the integration of the measured temperature in the mathematical algorithm automatically, semi-automatically and or manually.

DETAILED DESCRIPTION OF THE DRAWINGS

Figure 1:
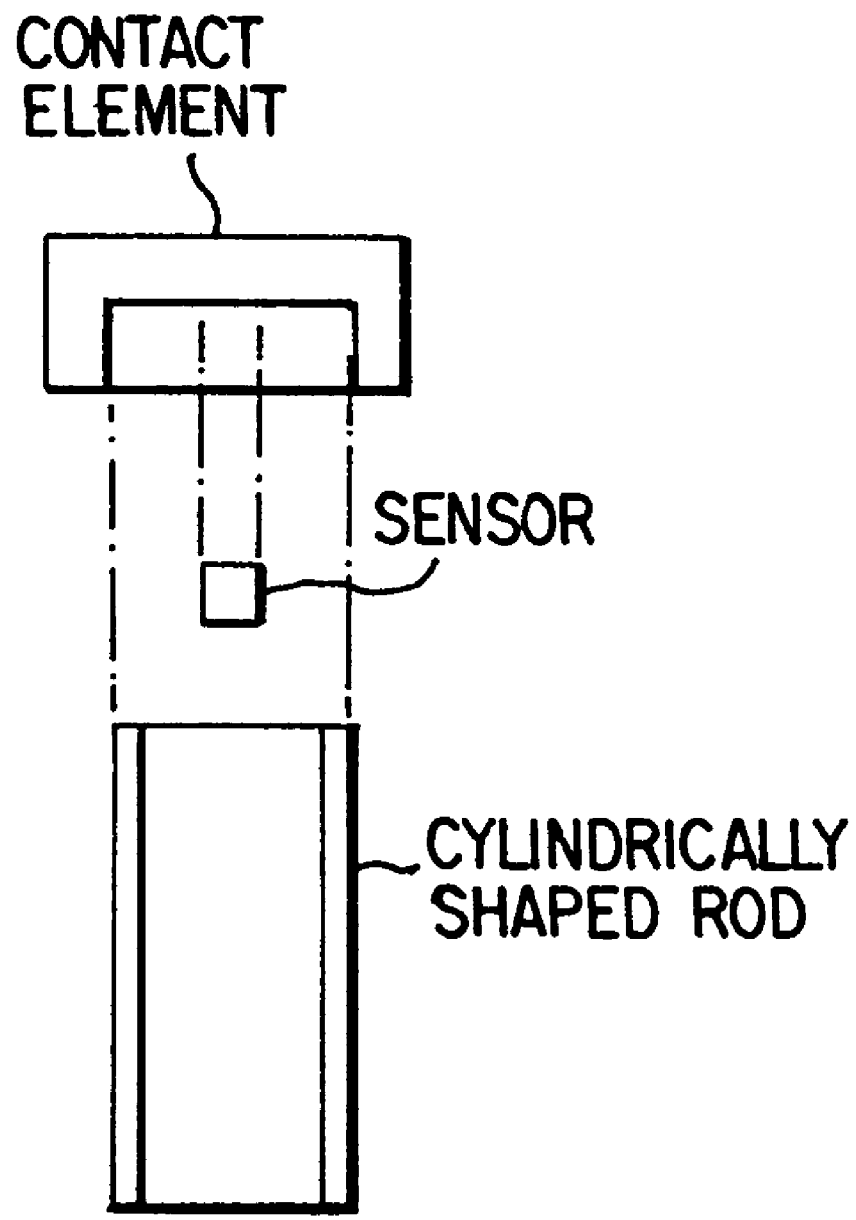
FIG. 1 is a schematic diagram of the sensor components according to the present invention.

Referring to FIG. 1, the sensor components for the contact measurement are composed of a cylindrically shaped rod having great heat resistance (material-polyvinyl chloride) and a contact section or element which possesses good heat conductivity and does not oxidize. A sensor, with the aid of which a thermal signal is converted into an electric signal, is attached beneath this contact section. The cylindrically shaped rod, on the one hand, serves as a mechanical holding unit for the contact section and, on the other hand, is an important element for thermography. It is to be noted that the connecting wires (not shown) of the sensor are conducted through the cylindrically shaped rod. The individual components are joined by means of modern adhesives as would be known by one skilled in the art.

The adhesive connection between the contact section and the cylindrically shaped rod is carried out in such a manner that neither fluids nor other materials are able to enter the sensor component from above. The bottom opening of the cylindrically shaped rod can be selectively closed with an adhesive.

Figure 3:
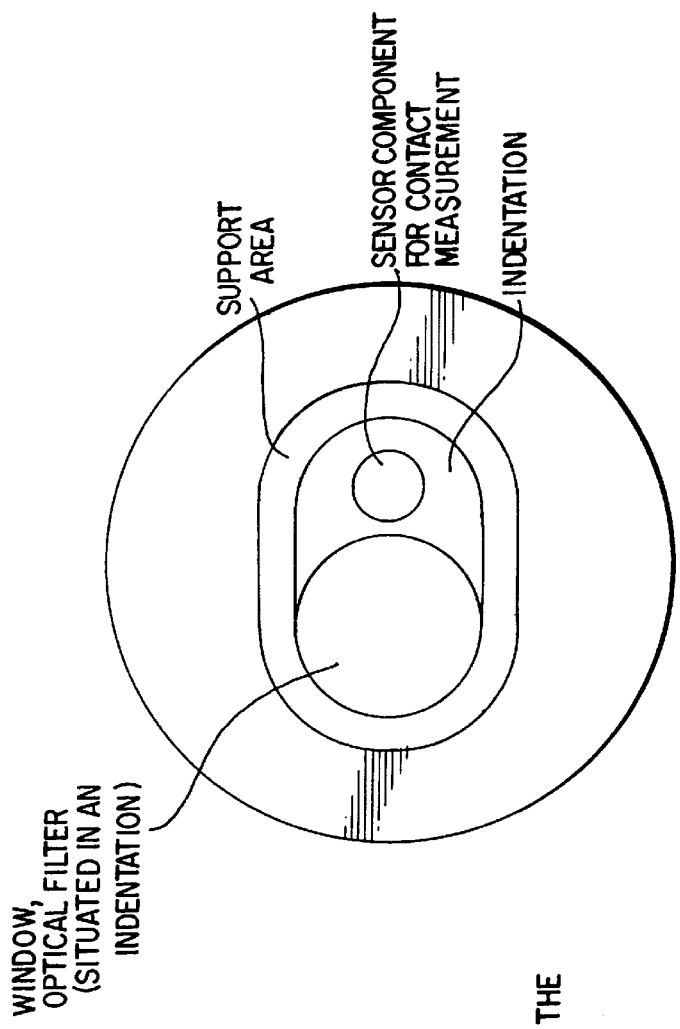
FIG. 3 is a top view of the measurement system according to the present invention.
Figure 2:
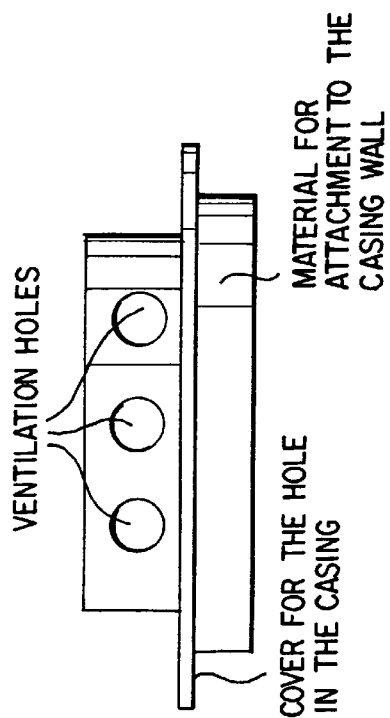
FIG. 2 is a side view of the measurement system according to the present invention.

In FIGS. 2 and 3, the cross section of the measurement system can be seen. Above the casing wall is a sensor body having the sensor component for contact measurement. The top part of the sensor component is composed, as can already be seen in FIG. 1, as follows: located beneath the circular area of the cylindrically shaped rod is a temperature sensor, i.e., e.g., an NTC resistor; attached above the circular area is a disk made of plastic for improved heat transmission; in the bottom region of the sensor body, another NTC resistor or sensor, which registers the weakened thermal energy, is located on the cylindrically shaped rod. For thermochromatography, e.g., one or more sensors are disposed on the cylindrically shaped rod, which is a part for the contact measurement.

By means of an indentation, space is created which can be irradiated without obstruction by heat rays radiating from the finger. The sensor (NTC resistor) serving to register the temperature is screened by filters and lenses made of germanium or silicon as well as by a shutter from the radiation source. A second sensor serves to register the air (as a reference value).

The configuration of the holding unit can be different. The NTC is held in this cavity in such a manner that contactless measurement of the heat radiation from the object to be measured is permitted. At a suitable site, the heat radiating from the object to be measured can be measured by means of heat conductivity.

Furthermore, the casing serves to protect the NTC from soiling and destruction.

A special electronic circuit converts the measured analog values with a resolution of 24 bits into digital data. This permits temperature measurements with resolutions <$10^{-4}$. A (one chip) microcomputer containing an evaluation algorithm compares the measured data with the stored calibration functions and allocates concentration values to specific temperature values.

The microcomputer conveys the processed data, provided in digital form, to a suitable display (liquid crystal display, monitor, etc.), which shows the determined glucose concentration as a numerical value (optionally in mg/dl or mol/l). While the microcomputer is not shown, one skilled in the art can readily adapt a processor to perform the recited functions based on the teachings contained herein.

Principle Description of the Mathematical Evaluation Algorithm

First, the invented device is calibrated. In order to do this, the relationship between the determined measured values and the glucose concentrations is ascertained in the form of a calibration, i.e., an analysis, function. First the to-be-evaluated measuring range, that is the signal portion relevant for the evaluation, is automatically detected with the aid of a function. This signal portion is composed of different values. The maximum and minimum value of these values is determined, and a statistical value for the evaluation is ascertained by means of substraction. In this manner, both the weakened thermal energy as well as the heat conductivity and heat radiation are ascertained and the data calculated in this manner are linked by means of a mathematical function and correlated with the glucose concentration. The reference (air) as well as the room temperature are taken into account in this procedure.

In summary, the procedure is as follows (greatly simplified): according to the measurement principle, a measurement procedure (sequentially or simultaneously; see above) delivers at least one, but preferably two or three, measurement values $T_{1i}$, $T_{2i}$ and $T_{3i}$. In addition, with each measurement procedure, the concentration of glucose in the blood has to be determined in the conventional manner (invasively). Measurement procedures, therefore, yield 3 measured values $T_{ni}$ and n glucose concentrations $c_n$. The concentrations $c_n$ are plotted against $T_{1i}$, $T_{2i}$ and $T_{3i}$. In this manner, three calibration functions are determined.

Moreover, an (or multiple) auxiliary function(s) is (are) determined in that, e.g., the three measured values $T_{1i}$, $T_{2i}$ and $T_{3i}$ are put into a relationship with respect to each other. The auxiliary function proves to be particularly useful in order to develop an analysis procedure which is free of matrix effects, and is therefore independent of the individual being tested.

The mathematical algorithm can e.g. be a linear regression procedure having one or more independent variables in a first or higher order forming a basis. In the process, a Fourier transformation may be utilized for the mathematical evaluation.

Thermal Analysis Methods

Thermography

Thermal analysis methods are among the most important techniques in examining minerals. The determination is based on the circumstance that both exothermic and endothermic processes occur in the case of structural changes. If a probe is heated together with a thermic inert standard, a specific temperature course is plotted. With the aid of a pair of thermoelements, a positive or a negative peak is registered. The position of the peak in the diagram is characteristic for the corresponding mineral. Likewise, e.g. a weight loss due to dehydration can also be determined by means of thermogravimetry, which is based on a similar principle. Thermal methods are combined with X-ray diffraction examinations or also IR-spectroscopy.

One procedure for thermographic diagnosis can be found in thermography. It is based on the fact that the thermal economy of a human being is unique to that individual and is oriented to the environment. Heat loss/absorption, as already described, can be reproduced under identical conditions. The number of papers dealing with the application of thermography in therapy control has hitherto still been small. An interfering factor for thermography is, e.g., room temperature.

The following is to be noted in ascertaining the heat radiation of an object. The IR pulses radiating from the surface of the body are registered by means of a specific detector, electronically amplified and can subsequently, on the one hand, be read directly and, on the other hand, recorded as a thermal image. In areas with reduced arterial blood circulation, the radiation is decreased. Hitherto, i.a., contact thermometers with liquid crystals have been used.

Like infrared thermography (IR-thermography), microwave thermography belongs to radiation thermometry. In contrast to IR-thermography, which only registers the skin temperature, microwave thermography also determines radiation of deeper tissue layers from the exterior.

IR thermography refers to measurement of temperature distributions in space. In IR-thermography there a two-dimensional temperature distribution is usually provided. A single quantum detector having minimal geometric dimensions is utilized as the measuring sensor. With the detector materials indium, antimonide, and mercury cadmium telluride being chiefly utilized in IR thermography, the prescribed limiting sensitivity, which is fixed by maximum exploitation of quanta, is almost reached in small wavelength intervals and cooling with liquid nitrogen. The physical relationship, with which to the temperature $T_i$ at every site in the measuring plane, the specific radiation flow density at the same site is distinctly allocated, has to be known. Thus, the thermodynamic state value temperature is distinctly linked to a radiation value.

Existence and knowledge of this relationship are the elementary preconditions for measuring the object temperatures with radiation detectors.

The optical components of the invented apparatus are usually fabricated out of IR-radiation permeable material such as, e.g., germanium or silicon. The surface is provided with antireflection coatings. The coating raises the IR-permeability of the detector to nearly 100%. Moreover, the statistical measurement device characteristic is also important. A measurement system suitable for IR-thermography has to ensure complete detection of radiation emitted from every site of the measured object. The advantages of both the plate thermography and the infrared thermography are that there is no radiation exposure and the measurements are noninvasive.

It is possible to utilize measurements in the microwave range of the electromagnetic spectrum. Pyroelectric detectors can also be used to detect thermal radiation. Moreover, a lock-in procedure may be used, which is a very common method to raise the sensitivity of an electronic signal. The signal-to-noise ratio may be raised by a certain factor and the signal amplitude may lie within a certain range. Measurements may be restricted to a defined wavelength range. All solid state liquids and gases, the thermal conductivity of which has a value larger than zero, are employed as receivers for heat radiation and heat conduction.

What is claimed is:

1. A process for qualitative and quantitive detection of thermal transmissions between a living body and a sensor via measurement processes for determining at least one of a temperature and temperature change using radiation sources and detectors both for contactless and contact measurement, the process comprising the steps of:

physically detecting with high precision thermal interactions within a thermodynamic system composed of the sensor, the living body, and any space arranged therebetween via a combination of said measurement processes;

electronically numerically converting the physically detected thermal interactions using a processor;

evaluating said electronically numerically converted thermal interactions via said processor; and assessing and unequivocally allocating the evaluated electronically numerically converted thermal interactions to a glucose concentration in human blood via a mathematical algorithm.

2. The process according to claim 1, wherein the physically detecting step detects heat radiated from at least one of a surface of the body in a layer close to the surface, in body cavities, in a deeper resolving manner such as via specific heat radiating from below the surface inside the living body, said heat being transmitted and radiated to said sensor such that measured data obtained thereby is unequivocally correlated to the glucose concentration in the human blood.

3. The process according to claim 1, wherein said thermal interactions between the living body and the sensor are relatively calculated using at least one reference value.

4. The process according to claim 3, wherein said thermal interactions are also calculated using data processing from temperature differences and temperature quotients, and from their mathematical conversions, derivations and integrals, wherein said thermal interactions are allocated via the mathematical algorithm unequivocally to the specific glucose concentration of the human blood.

5. The process according to claim 4, wherein said temperature differences and temperature quotients are obtained by applying at least one of the contact and contactless measurement process in as precise a manner as possible.

6. The process according to claim 1, further comprising the steps of:

utilizing measured values gained prior to and following measurements as blank values, and even directly as data for calibration and analysis for formation of temperature difference and/or temperature quotients.

7. The process according to claim 1, wherein at least one of a temperature difference and a temperature quotient is allocated to the glucose concentration, said temperature difference and temperature quotient not exceeding an amount of ±33K of the measured temperature in or on a casing of the sensor serving as a reference temperature.

8. The process according to claim 1, wherein a temperature measured at one or more specific and/or random sites in and on the sensor casing is utilized as a reference temperature for formation of at least one of a temperature difference and temperature quotient amount.

9. The process according to claim 1, wherein an air, gas, or vacuum temperature measured in/at the sensor casing is usable as a background temperature which is utilized as a reference temperature.

10. The process according to claim 9, wherein a respective background temperature is gained with the aid of the measured values made prior to and following measurements made by sensor heads of the sensor.

11. The process according to claim 1, wherein an interfering influence of room temperature is compensated as the temperature is integrated in the mathematical evaluation algorithm.

12. The process according to claim 11, wherein said compensation occurs one of automatically, semi-automatically, and manually.

13. The process according to claim 12, wherein a momentary temperature of the to be examined living body is integrated as a fixed value in said assessment and evaluation steps.

14. The process according to claim 1, wherein the analysis algorithm is controlled selectively dependent on, or independent of, the living bodies being measured.

15. The process according to claim 1, wherein the analyses results are determined matrix-effect-free independent of individuals with the aid of at least one main function and/or at least one or more auxiliary functions.

16. The process according to claim 1, wherein the mathematical algorithm is a linear regression procedure having one independent variable in a first or higher order forming a basis.

17. The process according to claim 1, wherein the mathematical algorithm is a linear regression procedure having two or more independent variables in a first or higher order forming a basis.

18. The process according to claim 1, wherein a temperature difference/quotient caused by and depending on a respective individual and his/her state of health is determined via an auxiliary function from two temperatures measured independently, simultaneously or time-staggered, spatially and/or time-resolved, and is applied as an individual compensation factor.

19. The process according to claim 1, wherein for evaluation, only temperature differences and/or temperature quotients caused by heat conduction or by weakened heat conduction or by heat radiation or a combination of all the determined thermal processes are utilized.

20. The process according to claim 1, wherein a measurement peak is detected automatically with the aid of a function.

21. The process according to claim 1, wherein only a relevant portion of the measurement signal is utilized for evaluation.

22. The process according to claim 21, wherein a minimal and maximum value of said relevant measurement signal portion is detected and the temperature difference and/or temperature quotient of both values are determined for said heat radiation as well as for said heat conduction and for said weakened heat conduction.

23. The process according to claim 1, wherein for said temperature difference and/or temperature quotient formation, the heat radiating from the human body transmitted via the contact surface of said sensor is completely determined, specifically or selectively for said temperature radiation, said heat conduction and said weakened heat conduction in and on said sensor casing, said heat being registered.

24. The process according to claim 1, wherein the heat radiating and/or emitting from the living body is separated according to its different nature thermoanalytically, according to wavelength or according to frequency.

25. The process according to claim 1, wherein a Fourier transformation is utilized for the mathematical evaluation.

26. The process according to claim 1, wherein heat radiation, for one or more than one specific frequency interval is integrated and said frequency interval is linked, independently of one another and/or dependent on each other, for evaluation by being pretreated in a suitable mathematical manner such as by being differentiated or integrated over time.

27. The process according to claim 1, wherein heat radiation in a wavelength range of 3–30 $\mu$m is measured.

28. The process according to claim 1, wherein sensitivity is improved using a lock-in procedure.

29. The process according to claim 28, wherein a signal amplitude is in the range of 1 $\mu$V to 10 mV.

30. The process according to claim 28, wherein a signal-to-noise ratio is raised by a factor of 1000.

31. The process according to claim 1, wherein semiconductor materials such as germanium or silicon are utilized as detectors for heat radiation and heat conduction in the sensor.

32. The process according to claim 1, wherein pyroelectric detectors are utilized as said detectors for heat radiation and heat conduction in the sensor.

33. The process according to claim 1, wherein all solid state liquids and gases, the thermal conductivity of which has a value larger than zero, are employed as receivers for heat radiation and heat conduction.

34. The process according to claim 1, wherein an interaction between the human body and the microwave radiation is exploited.

* * * * *